United States Patent [19]
Black et al.

[11] Patent Number: 5,534,527
[45] Date of Patent: Jul. 9, 1996

[54] METHODS FOR INHIBITING BONE LOSS BY TREATING WITH AROYLBENZOTHIOPHENES AND ESTROGEN

[75] Inventors: Larry J. Black, Indianapolis; George J. Cullinan, Trafalgar, both of Ind.

[73] Assignee: Eli Lilly and Company, Indianapolis, Ind.

[21] Appl. No.: 422,096

[22] Filed: Apr. 14, 1995

Related U.S. Application Data

[60] Continuation of Ser. No. 329,396, Oct. 26, 1994, Pat. No. 5,457,117, which is a division of Ser. No. 180,522, Jan. 12, 1994, Pat. No. 5,393,763, which is a continuation of Ser. No. 920,933, Jul. 28, 1992, abandoned.

[51] Int. Cl.$^6$ .......................... A61K 31/44; A61K 31/40
[52] U.S. Cl. ..................... 514/333; 514/422; 514/578; 514/443; 514/448
[58] Field of Search ................................ 514/333, 422, 514/578, 443, 448

[56] References Cited

U.S. PATENT DOCUMENTS

| | | | |
|---|---|---|---|
| 4,133,814 | 1/1979 | Jones et al. | 260/326.55 |
| 4,185,108 | 1/1980 | Samour et al. | 424/274 |
| 4,418,068 | 11/1983 | Jones | 424/267 |
| 4,729,999 | 3/1988 | Young | 514/227 |
| 4,894,373 | 1/1990 | Young | 514/239.2 |
| 4,970,237 | 11/1990 | Jensen et al. | 516/651 |
| 5,118,667 | 6/1992 | Adams et al. | 514/12 |
| 5,393,763 | 2/1995 | Black et al. | 514/333 |

FOREIGN PATENT DOCUMENTS 068563   1/1983   European Pat. Off. .

OTHER PUBLICATIONS

Williams, et al., *Journal of Bone and Mineral Research*, 6(1991).
FDC Reports, T&G 11, Mar. 30, 1992.
Jones, et al., *J. Med. Chem.*, 27, 1057–1066 (1984).
Feldmann, et al., *Bone and Mineral* 7, 245–254 (1989).
"Tamoxifen Trial Restricted", *SCRIP* No. 1702 Mar. 20, 1992, p. 22.
Jordan, et al., Breast Cancer Research Treatment, 10: 31–35 (1987).
Beall, et al., *Calcif Tissue Int.*, 36: 123–125 (1984).
Turner, et al., *Journal of Bone and Mineral Research* 2, No. 5, 449–456 (1987).
Williams, et al., *Bone and Mineral* 14, 205–220 (1991).
Turner et al., *Endocrinology*, 122, No. 3 1146–1150 (1988).
Love, et al., *The New England Journal of Medicine* 326, No. 13, 852–856 (1992).

*Primary Examiner*—Theodore J. Criares
*Attorney, Agent, or Firm*—James J. Sales

[57] ABSTRACT

The current invention provides methods and pharmaceutical formulations that are useful for inhibiting the loss of bone. These methods and formulations can be used without the associated adverse effects of estrogen therapy, and thus serve as an effective and acceptable treatment for osteoporosis.

1 Claim, No Drawings

METHODS FOR INHIBITING BONE LOSS BY TREATING WITH AROYLBENZOTHIOPHENES AND ESTROGEN

This application is a continuation of application Ser. No. 08/329,396, filed Oct. 26, 1994 now U.S. Pat. No. 4,457,117 which is a division of application Ser. No. 08/180,522 filed Jan. 12, 1994, now U.S. Pat. No. 5,393,763, which is a continuation of application Ser. No. 07/920,933 filed Jul. 28, 1992, now abandoned.

BACKGROUND OF THE INVENTION

This invention relates to the discovery that a group of 2-phenyl-3-aroylbenzothiophenes is useful in the prevention of bone loss.

The mechanism of bone loss is not well understood, but in practical effect, the disorder arises from an imbalance in the formation of new healthy bone and the resorption of old bone, skewed toward a net loss of bone tissue. This bone loss includes a decrease in both mineral content and protein matrix components of the bone, and leads to an increased fracture rate of, predominantly, femoral bones and bones in the forearm and vertebrae. These fractures, in turn, lead to an increase in general morbidity, a marked loss of stature and mobility, and, in many cases, an increase in mortality resulting from complications.

Bone loss occurs in a wide range of subjects, including post-menopausal women, patients who have undergone hysterectomy, patients who are undergoing or have undergone long-term administration of corticosteroids, patients suffering from Cushing's syndrome, and patients having gonadal dysgensis.

Unchecked, bone loss can lead to osteoporosis, a major debilitating disease whose prominent feature is the loss of bone mass (decreased density and enlargement of bone spaces) without a reduction in bone volume, producing porosity and fragility.

One of the most common types of osteoporosis is found in post-menopausal women affecting an estimated 20 to 25 million women in the United States alone. A significant feature of post-menopausal osteoporosis is the large and rapid loss of bone mass due to the cessation of estrogen production by the ovaries. Indeed, data clearly support the ability of estrogens to limit the progression of osteoporotic bone loss, and estrogen replacement is a recognized treatment for post-menopausal osteoporosis in the United States and many other countries. However, although estrogens have beneficial effects on bone, given even at very low levels, long-term estrogen therapy has been implicated in a variety of disorders, including an increase in the risk of uterine and breast cancer, causing many women to avoid this treatment. Recently suggested therapeutic regimens, which seek to lessen the cancer risk, such as administering combinations of progestogen and estrogen, cause the patient to experience regular withdrawal bleeding, which is unacceptable to most older women. Concerns over the significant undesirable effects associated with estrogen therapy, and the limited ability of estrogens to reverse existing bone loss, support the need to develop alternative therapy for bone loss that generates the desirable effects on bone but does not cause undesirable effects.

Attempts to fill this need by the use of compounds commonly known as antiestrogens, which interact with the estrogen receptor, have had limited success, perhaps due to the fact that these compounds generally display a mixed agonist/antagonist effect. That is, although these compounds can antagonize estrogen interaction with the receptor, the compounds themselves may cause estrogenic responses in those tissues having estrogen receptors. Therefore, some antiestrogens are subject to the same adverse effects associated with estrogen therapy.

The current invention provides methods for inhibiting the loss of bone without the associated adverse effects of estrogen therapy, and thus serves as an effective and acceptable treatment for osteoporosis.

The 2-phenyl-3-aroylbenzothiophene compounds that are the active component in the formulations and methods of this invention were first developed by C. David Jones and Tulio Suarez as anti-fertility agents (see U.S. Pat. No. 4,133,814, issued Jan. 9, 1979). Certain compounds in the group were found to be useful in suppressing the growth of mammary tumors.

Jones later found a group of related compounds to be useful for antiestrogen and antiandrogen therapy, especially in the treatment of mammary and prostatic tumors (see U.S. Pat. No. 4,418,068, issued Nov. 29, 1983). One of these compounds, the compound of formula I wherein X is a bond, R and $R^1$ are hydroxyl, and $R^2$ is a piperidino ring, was clinically tested for a brief time for the treatment of breast cancer. That compound is called raloxifene, formerly keoxifene.

SUMMARY OF THE INVENTION

This invention provides new methods for the treatment of bone loss comprising administering to a human in need of treatment an effective amount of a compound of formula I

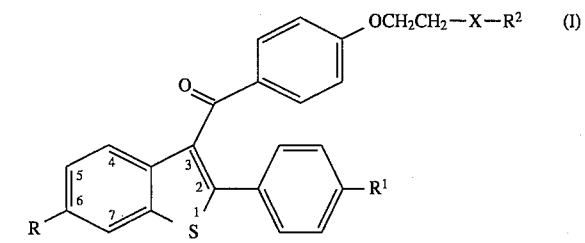

wherein
X is a bond, $CH_2$, or $CH_2CH_2$;
R and $R^1$, independently, are hydrogen, hydroxyl, $C_1$–$C_6$-alkoxy, $C_1$–$C_6$-acyloxy, $C_1$–$C_6$-alkoxy-$C_2$–$C_6$-acyloxy, $R^3$-substituted aryloxy, $R^3$-substituted aroyloxy, $R^4$-substituted carbonyloxy, chloro, or bromo;
$R^2$ is a heterocyclic ring selected from the group consisting of pyrrolidino, piperidino, or hexamethyleneimino;
$R^3$ is $C_1$–$C_3$-alkyl, $C_1$–$C_3$-alkoxy, hydrogen, or halo; and
$R^4$ is $C_1$–$C_6$-alkoxy or aryloxy; or
a pharmaceutically acceptable salt thereof.

The invention also provides pharmaceutical formulations for inhibiting bone loss comprising a compound of formula I, wherein R, R1, R2, and X are as defined above in an amount that increases or retains bone density, together with a pharmaceutically acceptable carrier.

DETAILED DESCRIPTION OF THE INVENTION

The current invention concerns the discovery that a group of 2-phenyl-3-aroylbenzothiophenes (benzothiophenes) of formula I are useful in the treatment of osteoporosis. The benzothiophenes of formula I inhibit the loss of bone that results from a lack of endogenous estrogen such as occurs in women following cessation of menstruation due to natural, surgical, or other processes. The reduction of bone density and mass that more rarely occurs in men is also tied to the loss of hormonal regulation and is therefore also a target for therapy according to the methods of the current invention.

The benzothiophenes of formula I are a series of nonsteroidal compounds that exhibit high affinity for conventional estrogen receptors in primary sex target tissues. However, they elicit minimal estrogenic responses in those tissues, and actually serve as potent antagonists of natural estrogens such as estradiol. In contrast to the report of Feldmann, S. et al., "Antiestrogen and antiandrogen administration reduce bone mass in the rat", *Bone and Mineral*, 7:245 (1989), the benzothiophenes of formula I are able to antagonize classical estrogenic responses in primary sex target tissues without significantly reducing bone density when given to intact or estrogen treated animals, and they prevent bone loss in estrogen deficient animals. This dichotomy indicates selective agonist/antagonist actions on specific target cells which would appear to be highly desirable in treatment of the menopausal syndrome. Accordingly, the real benefit of the current discovery is that the benzothiophenes of formula I inhibit the loss of bone but do not elicit significant estrogenic responses in the primary sex target tissues. Thus, the current invention provides a method of inhibiting bone loss comprising administering to a human in need of treatment an amount of a compound of formula I that inhibits bone loss but does not significantly affect the primary sex target tissues. This combination of features allows for long-term treatment of the chronic ailment with a diminished risk of developing the undesirable effects of customary estrogen replacement therapy.

The biological action of the benzothiophenes of formula I is complex and may be unrelated to the detectable presence of the parent compound in the blood. Following oral administration of a preferred benzothiophene of this invention, raloxifene (raloxifene hydrochloride), to human subjects in the clinic, the parent compound was not detected in the serum of those subjects. It was determined that following oral administration, the compound was extensively conjugated to the glucuronidated form and cleared quickly from the bloodstream. Although no biological endpoints were measured in the human recipients, there was concern that the compound was not bioavailable.

Experiments were undertaken to address the bioavailability issue in laboratory animals where biological activity could be assessed. The animal studies indicated that raloxifene was maximally active in inhibiting both uterine uptake of tritiated-estradiol and the normal uterotrophic response to estradiol even under conditions where raloxifene was extensively conjugated in the plasma of the animals. Moreover, the conjugate, isolated from the urine of human subjects treated with raloxifene, displayed significant antiestrogenic/antiuterotrophic activity when administered intravenously to rats, and inhibited the interaction of tritiated-estradiol with rat uterine estrogen receptors in a manner similar to the parent compound. These studies suggested the conjugated compound may have been converted to the parental form at the site of action, presumably by the action of β-glucuronidase. Such conversion may contribute to the activity of the compound. β-Glucuronidase is fairly ubiquitous and is thought to be active in the resorption process of bone remodeling, and would presumably be available for converting the conjugated compound to the parental form if required for activity. Therefore, conjugation of the benzothiophenes of formula I is not considered to be necessarily detrimental to their bioavailability as an inhibitor of bone loss.

Thus, the method of treatment provided by this invention is practiced by administering to a human in need of inhibition of bone loss, a dose of a compound of formula I or a pharmaceutically acceptable salt thereof, that is effective to inhibit bone loss. A particular benefit of this method is that it avoids potentially harmful and unacceptable estrogenic side effects. The inhibition of bone loss contemplated by the present method includes both medical therapeutic and/or prophylactic treatment, as appropriate.

The method also includes the administration of a compound of formula I given in combination with estrogen. The term estrogen as used herein refers to any compound which approximates the spectrum of activities of the naturally acting molecule which is commonly believed to be 17β-estradiol. Examples of such compounds include estriol, estrone, ethynyl estradiol, Premarin (a commercial preparation of conjugated estrogens isolated from natural sources—Ayerst), and the like. Again, due to the selective agonist/antagonist properties of the compounds of formula I, this combination provides for the full benefits of estrogen therapy without the concomitant adverse effects associated with estrogen therapy alone.

The general chemical terms used in the description of a compound of formula I have their usual meanings. For example, the term "$C_1$–$C_3$-alkyl" includes such groups as methyl, ethyl, propyl, and isopropyl.

The term "$C_1$–$C_6$-alkoxy" includes such groups as methoxy, ethoxy, propoxy, butoxy, pentyloxy, and hexyloxy and also includes branched chain structures such as, for example, isopropoxy and isobutoxy.

The term "$C_1$–$C_6$-acyloxy" includes methanoyloxy, ethanoyloxy, propanoyloxy, butanoyloxy, pentanoyloxy, hexanoyloxy, and the like and also includes branched chain structures such as, for example, 2,2-dimethylpropanoyloxy, and 3,3-dimethylbutanoyloxy.

The term "$C_1$–$C_6$-alkoxy-$C_2$–$C_6$-acyloxy" contemplates, for example, methoxyethanoyloxy, methoxypropanoyloxy, methoxybutanoyloxy, methoxypentanoyloxy, methoxyhexanoyloxy, ethoxyethanoyloxy, ethoxypropanoyloxy, ethoxybutanoyloxy, ethoxypentanoyloxy, ethoxyhexanoyloxy, propoxyethanoyloxy, propoxypropanoyloxy, propoxybutanoyloxy, and the like.

It should also be understood that as used herein, references to alkyl and alkoxy structures also include cycloalkyl and cycloalkoxy groups where the number of carbons within the structure is at least 3.

The terms "$R^3$-substituted aryloxy" and "$R^3$-substituted aroyloxy" include such groups as phenyloxy, thienyloxy, furyloxy, naphthyloxy, benzoyloxy, thienoyloxy, furoyloxy, naphthoyloxy, and the like, where the $R^3$ substitution group may be hydrogen, hydroxyl, $C_1$–$C_3$-alkyl, $C_1$–$C_3$-alkoxy, or halo.

The term "$R^4$-substituted carbonyloxy, where the $R^4$ substitution group may be $C_1$–$C_6$-alkoxy or aryloxy, includes carbonate structures such as methoxycarbonyloxy ethoxycarbonyloxy, propoxycarbonyloxy, butoxycarbonyloxy, pentyloxycarbonyloxy, hexyloxycarbonyloxy, phenyloxycarbonyloxy, thienyloxycarbonyloxy, furyloxycarbonyloxy, and naphthyloxycarbonyloxy.

Preferred methods of this invention comprise the use of compounds of formula I wherein R and $R^1$ are other than hydrogen, alkoxy, aryloxy, chloro, or bromo and therefore represent ester and carbonate configurations. Other preferred methods include the use of formula I compounds wherein R and $R^1$ are the same as one another. Certain $R^2$ groups also demonstrate preferable characteristics when used in the methods of this invention. For example, preferred methods of this invention include the use of formula I compounds wherein $R^2$ is piperidino or pyrrolidino, especially piperidino. A further preferred subgroup of the preferred piperidino and pyrrolidino compounds include compounds wherein R and $R^1$ are other than hydrogen and, in particular, those wherein R and $R^1$ are hydroxyl.

All of the compounds used in the methods of the current invention can be made according to established procedures, such as those detailed in U.S. Pat. No. 4,133,814 and U.S. Pat. No. 4,418,068. In general, the process starts with a benzo[b]thiophene having a 6-hydroxyl group and a 2-(4-hydroxyphenyl) group. The starting compound is protected, alkylated, and deprotected to form the formula I compounds wherein R and $R^1$ are both hydroxy. The formula I compounds that are ethers, esters, and carbonates may then be formed if desired. Examples of the preparation of such compounds are provided in the U.S. patents discussed above. Specific preparations of yet other derivatized compounds useful in the current invention are outlined in the Preparations sections below. Modifications to the above methods may be necessary to accommodate reactive functionalities of particular substituents. Such modifications would be both apparent to, and readily ascertained by, those skilled in the art.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methane-sulfonate, naphthalene-1-sulfonate, naphthalene-2-sulfonate, p-toluenesulfonate, xylenesulfonate, tartarate, and the like.

In addition, some of the formula I compounds may form solvates with water or organic solvents such as ethanol. These solvates are also contemplated for use in the methods of this invention.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates and bicarbonates, as well as aliphatic and aromatic amines, aliphatic diamines and hydroxy alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

The current invention also provides useful pharmaceutical formulations for inhibiting bone loss comprising a formula I compound plus one or more pharmaceutically acceptable excipients. Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to treat or inhibit bone loss according to this invention will depend upon the severity of the disease, its route of administration, and related factors that will be decided by the attending physician. Generally, accepted and effective doses will be from about 0.1 to about 1000 mg, and more typically from about 200 to about 600 mg. Such dosages will be administered to a subject in need of treatment from once to about three times each day, or more often as needed to effectively inhibit the bone loss process.

It is usually preferred to administer a compound of formula I in the form of an acid addition salt, as is customary in the administration of pharmaceuticals bearing a basic group such as the piperidino ring. It is also advantageous to administer such a compound by the oral route to an aging human (e.g. a post-menopausal female or a male showing evidence of bone loss by X-ray analysis). For such purposes the following oral dosage forms are available.

FORMULATIONS

In the formulations which follow, "Active ingredient" means a compound of formula I.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations containing raloxifene that have been made include those shown below:

Formulation 2: Raloxifene capsule

| Ingredient | Quantity (mg/capsule) |
| --- | --- |
| Raloxifene | 1 |
| Starch, NF | 112 |
| Starch flowable powder | 225.3 |
| Silicone fluid 350 centistokes | 1.7 |

Formulation 3: Raloxifene capsule

| Ingredient | Quantity (mg/capsule) |
| --- | --- |
| Raloxifene | 5 |
| Starch, NF | 108 |
| Starch flowable powder | 225.3 |
| Silicone fluid 350 centistokes | 1.7 |

Formulation 4: Raloxifene capsule

| Ingredient | Quantity (mg/capsule) |
| --- | --- |
| Raloxifene | 10 |
| Starch, NF | 103 |
| Starch flowable powder | 225.3 |
| Silicone fluid 350 centistokes | 1.7 |

Formulation 5: Raloxifene capsule

| Ingredient | Quantity (mg/capsule) |
| --- | --- |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 7: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Illustrative compounds that can be used in the formulations and methods of this invention are shown in Table 1.

TABLE 1

| Compound No. | X | R and $R^1$ | $R^2$ | Form |
| --- | --- | --- | --- | --- |
| 1 | bond | 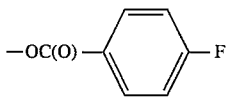 | piperidino | base |

TABLE 1-continued

| Compound No. | X | R and R¹ | R² | Form |
|---|---|---|---|---|
| 2 | bond | —OC(O)—⟨C₆H₄⟩—F | piperidino | HCl |
| 3 | bond | —OC(O)—cyclopropyl | piperidino | base |
| 4 | bond | —OC(O)—cyclopropyl | piperidino | HCl |
| 5 | bond | —OC(O)CH₂CH₂CH₃ | piperidino | base |
| 6 | bond | —OC(O)CH₂CH₂CH₃ | piperidino | HCl |
| 7 | bond | —OC(O)C(CH₃)₃ | piperidino | base |
| 8 | bond | —OC(O)C(CH₃)₃ | piperidino | HCl |
| 9 | bond | —OC(O)CH₂C(CH₃)₃ | piperidino | base |
| 10 | bond | —OC(O)CH₂C(CH₃)₃ | piperidino | HCl |
| 11 | bond | —OC(O)—⟨C₆H₄⟩—CH₃ | piperidino | HCl |
| 12 | bond | —OC(O)O—⟨C₆H₅⟩ | piperidino | base |
| 13 | bond | —OC(O)OCH₂CH₂CH₂CH₃ | piperidino | base |
| 14 | bond | —OC(O)OCH₂CH₂CH₂CH₃ | piperidino | HCl |
| 15 | bond | —OC(O)O—⟨C₆H₅⟩ | piperidino | base |
| 16 | bond | —OC(O)O—⟨C₆H₅⟩ | piperidino | HCl |
| 17 | bond | —OC(O)—naphthyl | piperidino | base |
| 18 | bond | —OC(O)CH₂CH₂OCH₃ | piperidino | base |
| 19 | bond | —OC(O)CH₂CH₂OCH₃ | piperidino | HCl |
| 20 | bond | OH | piperidino | base |
| 21 | bond | OH | piperidino | HCl |
| 22 | bond | H | piperidino | base |
| 23 | CH₂ | OH | piperidino | HCl |
| 24 | CH₂CH₂ | OH | piperidino | HCl |
| 25 | CH₂ | H | piperidino | HCl |
| 26 | bond | OH | pyrrolodino | base |
| 27 | bond | OH | pyrrolodino | HCl |
| 28 | CH₂ | OH | pyrrolodino | HCl |
| 29 | CH₂CH₂ | OH | pyrrolodino | HCl |
| 30 | bond | H | pyrrolodino | HCl |
| 31 | bond | OH | hexamethyleneimino | HCl |
| 32 | CH₂ | OH | hexamethyleneimino | HCl |
| 33 | CH₂CH₂ | OH | hexamethyleneimino | HCl |
| 34 | bond | OCH₃ | piperidino | HCl |

In the following Preparations, the compound numbers correspond to those given in Table 1

PREPARATION 1

Preparation of Compound 1:

6-(4-Fluorobenzoyloxy)-2-[4-(4-fluorobenzoyloxy) phenyl]benzo[b]thien-3-yl-[4-[2-(piperidin-1-yl) ethoxy]phenyl]methanone.

Raloxifene, 6-hydroxy-2-(4-hydroxyphenyl)benzo[b] thien-3-yl-4-[2-(piperidin-1-yl)ethoxyphenyl]methanone hydrochloride, (5.1 g, 10 mmol) was suspended in 250 mL of dry tetrahydrofuran (THF) and 7.1 g (70 mmol) of triethylamine, and approximately 10 mg of 4-(N,N-dimethylamino)pyridine were added. The suspension was cooled in an ice bath and placed under an atmosphere of nitrogen. 4-Fluorobenzoyl chloride (4.75 g, 30 mmol), dissolved in 20 mL of dry THF, was slowly added over a twenty minute period. The reaction mixture was stirred and allowed to slowly warm to room temperature over a period of eighteen hours. It was then filtered, and the filtrate was evaporated to a gum in vacuo. The crude product thus obtained was dissolved in a small volume of chloroform and chromotagraphed (HPLC) on a silica gel column eluted with a linear gradient of solvent, starting with chloroform and ending with a mixture of chloroform-methanol (19:1 (v/v)). The fractions containing the desired product as determined by thin layer chromatography (silica, chloroform-methanol (9:1)) were combined and evaporated to a gum. The final product was crystallized from ether to give 3.21 g of compound 1.

PMR: consistent with the structure

FDMS: m/e=717 M+

Elemental Analysis for $C_{42}H_{33}F_2NO_6S$: Theor: C, 70.29; H, 4.60; N, 1.95 Found: C, 70.05; H, 4.60; N, 1.89 Mol. Wt.: 717

PREPARATION 2

Preparation of Compound 2:

6-(4-Fluorobenzoyloxy)-2-[4-(4-fluorobenzoyloxy)- phenyl]benzo[ b]thien-3-yl-[4-[2-(piperidin-1-yl)ethoxy]-phenyl] methanone hydrochloride.

Compound 1 (5.15 g, 7.18 mmol) was dissolved in 25 mL THF, and 150 mL ether was added. Dry HCl gas was bubbled into the solution, and a white gummy precipitate formed. The liquid was removed by decanting, and the residue was crystallized from ethyl acetate with a small amount of ethanol added to effect solution. The product was filtered, washed with ether, and dried to give 4.41 g of Compound 2. as a white powder.

PMR: consistent with the structure

Elemental Analysis for $C_{42}H_{34}ClF_2NO_6S$: Theor: C, 66.88; H, 4.54; N, 1.86 Found: C, 66.59, H, 4.39; N, 1.60 Mol. Wt.: 753.5

PREPARATION 3

Preparation of Compound 3:

6-(Cyclopropylcarbonyloxy)-2-[4- (cyclopropylcarbonyloxy)phenyl]benzo[b]thien-3-yl- [4-[2-(piperidin-1-yl)ethoxy]phenyl]methanone.

The title compound was prepared using procedures analogous to those in Preparation 1, but using cyclopropylcarbonyl chloride, except that the product was not crystallized.

Yield=2.27 g.

PMR: consistent with the structure

FDMS: m/e=610 M+

PREPARATION 4

Preparation of Compound 4:

6-(Cyclopropylcarbonyloxy)-2-[4- (cyclopropylcarbonyloxy)phenyl]benzo[b]thien-3-yl- [4-[2-(piperidin-1-yl)ethoxy]phenyl]methanone hydrochloride.

Compound 4 was prepared from Compound 3 as described in Preparation 2.

PREPARATION 5

Preparation of Compound 5:

6-(n-Butanoyloxy)-2-[4-(n-butanoyloxy)phenyl] benzo[b]thien- 3-yl-[4-[2-(piperidin-1-yl)ethoxy]phenyl]methanone.

Compound 5 was prepared using the method of Preparation 1, but starting with n-butanoyl chloride, to give 4.12 g of final product as an oil.

PMR: consistent with the structure

FDMS: m/e=614 ($M^{+1}$)

PREPARATION 6

Preparation of Compound 6:

6-(n-Butanoyloxy)-2-[4-(n-butanoyloxy)phenyl] benzo[b]thien- 3-yl-[4-[2-(piperidin-1-yl)ethoxy]phenyl]methanone hydrochloride.

Compound 5 (4.12 g) was dissolved in ethyl acetate (50 mL), and a solution of HCl in ether was added until the precipitation stopped. The liquid was decanted off, and the white, gummy residue was triturated with diethyl ether and filtered. The residue was dried to give 1.33 g of Compound 6.

PMR: consistent with the structure

Elemental Analysis of for $C_{36}H_{40}ClNO_6S$: Theor.: C, 66.50; H, 6.20; N, 2.15 Found: C, 66.30; H, 6.28; N, 1.98 Mol. Wt.: 650.24

PREPARATION 7

Preparation of Compound 7:

6- (2,2-Dimethylpropanoyloxy)-2-[4-(2,2- dimethylpropanoyloxy)phenyl] benzo[b]thien-3-yl-[4-[2-(piperidin-1-yl)ethoxy]phenyl] methanone.

Compound 7 was prepared using the procedure of Preparation 1, but using 2,2-dimethylpropanoyl chloride.

PREPARATION 8

Preparation of Compound 8:

6-(2,2-Dimethylpropanoyloxy)-2-[4-(2,2-dimethylpropanoyloxy)phenyl]benzo[b]thien-3-yl-[4-[2-(piperidin-1-yl)ethoxy]phenyl]methanone hydrochloride.

Compound 8 was prepared from Compound 7, as described in Preparation 2.

FDMS: m/e=641 (M-HCl-1)

Elemental Analysis of $C_{38}H_{44}ClNO_6S$: Theor.: C, 67.29; H, 6.54; N, 2.07 Found: C, 67.02; H, 6.54; N, 1.90 Mol. Wt.: 678.29

PREPARATION 9

Preparation of Compound 9:

6-(3,3-Dimethylbutanoyloxy)-2-[4-(3,3-dimethylbutanoyloxy)phenyl]benzo[b]thien-3-yl[4-[2-(piperidin-1-yl)ethoxy]phenyl]methanone.

Compound 9 was prepared using the procedures of Preparation 1, but with 3,3-dimethylbutanoyl chloride.

PREPARATION 10

Preparation of Compound 10:

6-(3,3-Dimethylbutanoyloxy)-2-[4-(3,3-dimethylbutanoyloxy)phenyl]benzo[b]thien-3-yl[4-[2-(piperidin-1-yl)ethoxy]phenyl]methanone hydrochloride.

Compound 10 was prepared from Compound 9 as described in Preparation 2.

FDMS: m/e=669 (M-HCl-1)

Elemental Analysis of $C_{40}H_{48}ClNO_6S$: Theor.: C, 68.02; H, 6.85; N, 1.98 Found: C, 67.75; H, 6.83; N, 2.04 Mol. Wt.: 706.35

PREPARATION 11

Preparation of Compound 11:

6-(4-Methylbenzoyloxy)-2-[4-(4-methylbenzoyloxy)phenyl]benzo[b]thien-3-yl[4-[2-(piperidin-1-yl)ethoxy]phenyl]methanone hydrochloride.

Compound 11 was prepared from the free base using a procedure similar to that off Preparation 2.

FDMS: m/e=710 (H-HCl-1)

Elemental Analysis of $C_{44}H_{40}ClNO_6S$: Theor.: C, 70.81; H, 5.39; N, 1.88 Found: C, 71.10; H, 5.39; N, 1.94 Mol. Wt.: 746.33

PREPARATION 12

Preparation of Compound 12:

6-Benzoyloxy-2-[4-benzoyloxy)phenyl]benzo[b]thien-3-yl[4-[2-(piperidin-1-yl)ethoxy]-phenyl]methanone.

Compound 12 was prepared from the appropriate acid chloride as described in Preparation 1.

FDMS: m/e=682 (M+1)

Elemental Analysis of $C_{42}H_{35}NO_6S$: Calc: C, 73.80; H, 5.14; N, 2.05 Found: C, 73.27; H, 5.27; N, 1.94 Mol. Wt.: 681.8

PREPARATION 13

Preparation of Compound 13:

6-(n-Butoxyoyloxy)-2-[4(n-butoxyoyloxy)phenyl]benzo[b]thien-3-yl[4-[2-(piperidin-1-yl)ethoxy]phenyl]methanone.

Compound 13 was prepared in a manner analogous to that described in Preparation 1, except that n-butylchloroformate was used in place of the acid chloride. Yield=6.13 g in form of oil.

PMR: consistent with structure

FDMS: m/e=674 (M+1)

PREPARATION 14

Preparation of Compound 14:

6-(n-Butoxycarbonyloxy)-2-[4(n-butoxycarbonyloxy)phenyl]benzo[b]thien-3-yl[4-[2-(piperidin-1-yl)ethoxy]phenyl]methanone hydrochloride.

Compound 13 was converted to the hydrochloride salt in a manner analogous to that described in Preparation 6.

PMR: consistent with structure

Elemental Analysis of $C_{38}H_{44}ClNO_8S$: Calc: C, 64.26; H, 6.24; N, 1.97 Found: C, 63.97; H, 6.34; N, 1.98 Mol. Wt.: 710.29

PREPARATION 15

Preparation of Compound 15:

6-(Phenyloxycarbonyloxy)-2-[4(phenyloxycarbonyloxy)phenyl]benzo[ b]thien-3-yl[4-[2-(piperidin-1-yl)ethoxy]phenyl]methanone.

This compound was prepared in a manner analogous to that described in Preparation 13, but using the appropriate acyl ester. Yield=3.59 g of final product as a tan amorphous powder.

PMR: consistent with structure

FDMS: m/e=713 (M+)

PREPARATION 16

Preparation of Compound 16:

6-(Phenyloxycarbonyloxy)-2-[4(phenyloxycarbonyloxy)phenyl]benzo[b]thien-3-yl[4-[2-(piperidin-1-yl)ethoxy]phenyl]methanone hydrochloride.

Compound 15 was converted to the hydrochloride salt in a manner analogous to that described in Preparation 6.

PMR: consistent with structure

Elemental Analysis of $C_{38}H_{44}ClNO_8S$: Calc: C, 67.24; H, 4.84; N, 1.87 Found: C, 66.94; H, 4.96; N, 1.84 Mol. Wt.: 750.27

PREPARATION 17

Preparation of Compound 17:

6-(Naphthoyloxy)-2-[4(1-naphthoyloxy)phenyl]benzo[b]thien-3-yl[4-[2-(piperidin-1-yl)ethoxy]phenyl]methanone.

Compound 17 was prepared as described in Preparation 1 using the appropriate acid halide. Yield=3.5 g of a white amorphous powder PMR: consistent with structure FDMS: m/e=781 (M+)

Elemental Analysis of $C_{50}H_{39}NO_6S$: Calc: C, 76.80; H, 5.03; N, 1.79 Found: C, 76.53; H, 5.20; N, 1.53 Mol. Wt.: 781.94

PREPARATION 18

Preparation of Compound 18:

6-(Methoxyethanoyloxy)-2-[4(methoxyethanoyloxy)phenyl]benzo[b]thien-3-yl[4-[2-(piperidin-1-yl)ethoxy]phenyl]methanone.

Compound 18 was prepared as described in Preparation 1 using the appropriate acid halide. Yield=3.61 g of a gummy solid.

PMR: consistent with structure

FDMS: m/e=618 (M+1)

PREPARATION 19

Preparation of Compound 19:

6-(Methoxyethanoyloxy)-2-[4(methoxyethanoyloxy)phenyl]benzo[b]thien-3-yl[4-[2-(piperidin-1-yl)ethoxy]phenyl]methanone hydrochloride.

Compound 19 was prepared from 3.5 g of Compound 18 as described in Preparation 2. Yield=1.65 g of amorphous white powder.

PMR: consistent with structure

FDMS: m/e=618 (M+1)

Elemental Analysis of $C_{34}H_{36}NO_8S$: Calc: C, 62.43; H, 5.55; N, 2.14 Found: C, 62.23; H, 5.63; N, 2.15

The following nonlimiting examples illustrate the methods and formulations of this invention.

EXAMPLE 1

In the examples illustrating the methods, a model of post-menopausal osteoporosis was used in which effects of different treatments upon femur density were determined.

Seventy-five day old female Sprague Dawley rats (weight range of 225 to 275 g) were obtained from Charles River Laboratories (Portage, Mich.). They were housed in groups of 3 and had ad libitum access to food (calcium content approximately 1%) and water. Room temperature was maintained at 22.2°±1.7° C. with a minimum relative humidity of 40%. The photoperiod in the room was 12 hours light and 12 hours dark.

One week after arrival, the rats underwent bilateral ovariectomy under anesthesia (44 mg/kg Ketamine and 5 mg/kg Xylazine (Butler, Indianapolis, Ind.) administered intramuscularly). Treatment with vehicle, estrogen, or a compound of formula I was initiated on the day of surgery following recovery from anesthesia. Oral dosage was by gavage in 0.5 mL of 1% carboxymethylcellulose (CMC). Body weight was determined at the time of surgery and weekly thereafter and the dosage was adjusted with changes in body weight. Vehicle or estrogen treated ovariectomized (ovex) rats and non-ovariectomized (intact) rats were evaluated in parallel with each experimental group to serve as negative and positive controls.

The rats were treated daily for 35 days (6 rats per treatment group) and sacrificed by decapitation on the 36th day. The 35 day time period was sufficient to allow maximal reduction in bone density, measured as described herein. At the time of sacrifice, the uteri were removed, dissected free of extraneous tissue, and the fluid contents were expelled before determination of wet weight in order to confirm estrogen deficiency associated with complete ovariectomy. Uterine weight was routinely reduced about 75% in response to ovariectomy. The uteri were then placed in 10% neutral buffered formalin to allow for subsequent histological analysis.

The right femurs were excised and scanned at the distal metaphysis 1 mm from the patellar groove with single photon absorptiometry. Results of the densitometer measurements represent a calculation of bone density as a function of the bone mineral content and bone width.

INFLUENCE OF RALOXIFENE ON BONE DENSITY

The results of control treatments from five separate experiments are accumulated in Table 2. In summary, ovariectomy of the rats caused a reduction in femur density of about 25% as compared to intact vehicle treated controls. Estrogen, administered in the orally active form of ethynyl estradiol ($EE_2$), prevented this loss of bone in a dose dependent manner, but it also exerted a stimulatory action on the uterus resulting in uterine weights approaching that of an intact rat when administered at 100 µg/kg. Results are reported as the mean of measurements from thirty rats±the standard error of the mean.

In these studies, raloxifene also prevented bone loss in a dose dependent manner; however, only minimal increase of uterine weight over the ovariectomized controls was present in these animals. The results of five assays using raloxifene are combined in Table 3. Accordingly, each point reflects the responses of thirty rats and depicts a typical dose response curve for raloxifene in this model. Results are reported as the mean±the standard error of the mean.

TABLE 2

|  | Bone Density (mg/cm/cm) | Uterine Weight (mg) |
| --- | --- | --- |
| Ovariectomy control (0.5 mL CMC oral) | 170 ± 3 | 127 ± 5 |
| Intact control (0.5 mL CMC oral) | 220 ± 4 | 545 ± 19 |
| $EE_2$ 100 µg/kg, oral | 210 ± 4 | 490 ± 11 |

TABLE 3

|  | Bone Density (mg/cm/cm) | Uterine Weight (mg) |
| --- | --- | --- |
| Ovariectomy control (0.5 mL CMC oral) | 171 ± 3 | 127 ± 5 |

TABLE 3-continued

|  | Bone Density (mg/cm/cm) | Uterine Weight (mg) |
|---|---|---|
| Intact control (0.5 mL CMC oral) | 222 ± 3 | 540 ± 22 |
| raloxifene 0.01 mg/kg, oral | 176 ± 3 | 150 ± 5 |
| raloxifene 0.10 mg/kg, oral | 197 ± 3 | 196 ± 5 |
| raloxifene 1.00 mg/kg, oral | 201 ± 3 | 199 ± 5 |
| raloxifene 10.00 mg/kg, oral | 199 ± 3 | 186 ± 4 |

EXAMPLE 2

Raloxifene was administered alone or in combination with ethynyl estradiol. Rats treated with raloxifene alone had uterine weights which were marginally higher than the ovariectomized controls and much less than those of ethynyl estradiol treated rats, which approached those of the intact controls. Conversely, raloxifene treatment significantly reduced bone loss in ovariectomized rats, and when given in combination with ethynyl estradiol it did not appreciably reduce the protective effect of the estrogen on bone density. The results are shown in Table 4.

TABLE 4

|  | Bone Density (mg/cm/cm) | Uterine Weight (mg) |
|---|---|---|
| Experiment A |  |  |
| Ovariectomy control (0.5 mL CMC oral) | 162 ± 4 | 142 ± 18 |
| Intact control (0.5 mL CMC oral) | 219 ± 5 | 532 ± 49 |
| EE$_2$ 100 µg/kg, oral | 202 ± 6 | 450 ± 17 |
| EE$_2$ 100 µg/kg + raloxifene 0.10 mg/kg, oral | 204 ± 2 | 315 ± 10 |
| EE$_2$ 100 µg/kg + raloxifene 1 mg/kg, oral | 200 ± 5 | 250 ± 21 |
| Experiment B |  |  |
| Ovariectomy control (0.5 mL CMC oral) | 165 ± 8 | 116 ± 6 |
| Intact control (0.5 mL CMC oral) | 220 ± 4 | 605 ± 69 |
| EE$_2$ 100 µg/kg, oral | 215 ± 11 | 481 ± 24 |
| raloxifene 1 mg/kg + EE$_2$ 100 µg/kg, oral | 197 ± 7 | 263 ± 17 |
| raloxifene 1 mg/kg | 198 ± 11 | 202 ± 5 |

EXAMPLE 3

The ability of raloxifene to inhibit bone loss was compared to that of tamoxifen (SIGMA, St. Louis, Mo.). Tamoxifen, a well known antiestrogen currently used in the treatment of certain cancers, has been shown to inhibit bone loss (see for example, Love, R., et al. 1992 "Effects of tamoxifen on bone mineral density in postmenopausal women with breast cancer", N Eng J Med 326:852; Turner, R., et al. 1988 "Tamoxifen inhibits osteoclast-mediated resorption of trabecular bone in ovarian hormone-deficient rats", Endo 122:1146). A relatively narrow range of doses of raloxifene and tamoxifen was administered orally to ovariectomized rats as in the previous example. Although both of these agents displayed the ability to prevent reduction of femur density while evoking only modest uterotrophic activity, as identified by gains in uterine weight (Table 5), a comparison of several histological parameters demonstrated a marked difference between the rats treated with these agents (Table 6).

Increases in epithelial height are a sign of estrogenicity of therapeutic agents and may be associated with increased incidence of uterine cancer. When raloxifene was administered as described in Example 1, only at one dose was there any statistically measurable increase in epithelial height over the ovariectomized controls. This was in contrast to the results seen with tamoxifen and estrogen. At all doses given, tamoxifen increased epithelial height equal to that of an intact rat, about a six-fold increase over the response seen with raloxifene. Estradiol treatment increased epithelial height to a thickness greater than intact rats.

Estrogenicity was also assessed by evaluating the adverse response of eosinophil infiltration into the stromal layer of the uterus (Table 6). Raloxifene did not cause any increase in the number of eosinophils observed in the stromal layer of ovariectomized rats while tamoxifen caused a significant increase in the response. Estradiol, as expected, caused a large increase in eosinophil infiltration.

Little or no difference was detectable between raloxifene and tamoxifen effects on thickness of the stroma and myometrium. Both agents caused an increase in these measurements that was much less than the effect of estrogen.

A total score of estrogenicity, which was a compilation of all four parameters, showed that raloxifene was significantly less estrogenic than tamoxifen.

TABLE 5

|  | Bone Density (mg/cm/cm) | Uterine Weight (mg) |
|---|---|---|
| Ovariectomy control (0.5 mL CMC oral) | 171 ± 5 | 126 ± 17 |
| Intact control (0.5 mL CMC oral) | 208 ± 4 | 490 ± 6 |
| EE$_2$ 100 µg/kg, oral | 212 ± 10 | 501 ± 37 |
| raloxifene 1 mg/kg, oral | 207 ± 13 | 198 ± 9 |
| tamoxifen 1 mg/kg, oral | 204 ± 7 | 216 ± 18 |

TABLE 6

|  | Epithelial Height | Stromal Eosinophils | Myometrial Thickness | Stromal Expansion |
|---|---|---|---|---|
| Ovariectomy control (0.5 mL CMC oral) | 1.24 | 1.00 | 4.42 | 10.83 |
| Intact control (0.5 mL CMC oral) | 2.71 | 4.17 | 8.67 | 20.67 |
| EE$_2$ 100 µg/kg, oral | 3.42 | 5.17 | 8.92 | 21.17 |
| raloxifene 1 mg/kg | 1.67 | 1.17 | 5.42 | 14.00 |
| tamoxifen 1 mg/kg | 2.58 | 2.83 | 5.50 | 14.17 |

EXAMPLE 4

Other compounds of formula I were administered orally in the rat assay described in Example 1. Table 7 reports the effect of a 1 mg/kg dose of each compound in terms of a percent inhibition of bone loss and percent uterine weight gain.

TABLE 7

| Compound Number | % Inhibition of Bone Loss[a] | % Uterine Weight Gain[b] |
|---|---|---|
| 2 | 86 | 26 |
| 6 | 24 | 19 |
| 8 | 66 | 24 |
| 10 | 52 | 24 |
| 11 | 26 | 28 |
| 12 | 60 | 15 |
| 14 | 121 | 32 |
| 16 | 108 | 25 |
| 18 | 21 | 17 |
| 27 | 25 | 1 |
| 34 | 26 | −6 |

[a]Percent inhibition of bone loss = (bone density of treated ovex animals − bone density of untreated ovex animals) ÷ (bone density of estrogen treated ovex animals − bone density of untreated ovex animals) × 100.
[b]Percent uterine weight gain = (uterine weight of treated ovex animals − uterine weight of ovex animals) ÷ (uterine weight of estrogen treated ovex animals − uterine weight of ovex animals) × 100.

EXAMPLE 5

Fracture rate as a consequence of osteoporosis is inversely correlated with bone mineral density. However, changes in bone density occur slowly, and are measured meaningfully only over many months or years. It is possible, however, to demonstrate that the formula I compounds, such as raloxifene, have positive effects on bone mineral density and bone loss by measuring various quickly responding biochemical parameters that reflect changes in skeletal metabolism. To this end, in a current test study of raloxifene at least one hundred-sixty patients are enrolled and randomized to four treatment groups: estrogen, two different doses of raloxifene, and placebo. Patients are treated daily for eight weeks.

Blood and urine are collected before, during, and at the conclusion of treatment. In addition, an assessment of the uterine epithelium is made at the beginning and at the conclusion of the study. Estrogen administration and placebo serve as the positive and negative controls, respectively.

The patients are healthy post-menopausal (surgical or natural) women, age 45–60 who would normally be considered candidates for estrogen replacement in treatment for osteoporosis. This includes women with an intact uterus, who have had a last menstrual period more than six months, but less than six years in the past.

Patients who have received any of the following medications systematically at the beginning of the study are excluded from the study: vitamin D, corticosteroids, hypolipidemics, thiazides, antigout agents, salicylates, phenothiazines, sulfonates, tetracyclines, neomycin, and antihelmintics. Patients who have received any estrogen, progestin, or androgen treatment more recently than three months prior to the beginning of the study; patients who have ever received calcitonin, fluoride, or bisphosphonate therapy; patients who have diabetes mellitus; patients who have a cancer history anytime within the previous five years; patients with any undiagnosed or abnormal genital bleeding; patients with active, or a history of, thromboembolic disorders; patients who have impaired liver or kidney function; patients who have abnormal thyroid function; patients who are poor medical or psychiatric risks; or patients who consume an excess of alcohol or abuse drugs.

Patients in the estrogen treatment group receive 0.625 mg/day and the two raloxifene groups receive dosages of 200 and 600 mg/day, all groups receiving oral capsule formulations. Calcium carbonate, 648 mg tablets, is used as calcium supplement with all patients taking 2 tablets each morning during the course of the study.

The study is a double-blind design. The investigators and the patients do not know the treatment group to which the patient is assigned.

A baseline examination of each patient includes quantitative measurement of urinary calcium, creatinine, hydroxyproline, and pyridinoline crosslinks. Blood samples are measured for serum levels of osteocalcin, bone-specific alkaline phosphatase, raloxifene, and raloxifene metabolites. Baseline measurements also include examination of the uterus including uterine biopsy.

During subsequent visits to the investigating physician, measurements of the above parameters in response to treatment are repeated. The biochemical markers listed above that are associated with bone resorption have all been shown to be inhibited by the administration of estrogen as compared to an untreated individual. Raloxifene is also expected to inhibit the markers in estrogen deficient individuals as an indication that raloxifene is effective in inhibiting bone loss from the time that treatment is begun.

Subsequent longer term studies can incorporate the direct measurement of bone density by the use of a photon absorptiometry and the measurement of fracture rates associated with therapy.

We claim:

1. A pharmaceutical formulation comprising an effective amount of a compound of formula I

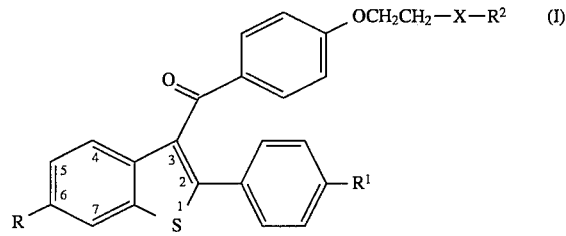

wherein

X is a bond, $CH_2$, or $CH_2CH_2$;

R and $R^1$, independently, are hydrogen, hydroxyl, $C_1$–$C_6$-alkoxy, $C_1$–$C_6$-acyloxy, $C_1$–$C_6$-alkoxy-$C_2$–$C_6$-acyloxy, $R^3$-substituted aryloxy, $R^3$-substituted aroyloxy, $R^4$-substituted carbonyloxy, chloro, or bromo;

$R^2$ is a heterocyclic ring selected from the group consisting of pyrrolidino, piperidino, or hexamethyleneimino;

$R^3$ is $C_1$–$C_3$-alkyl, $C_{1-C3}$-alkoxy, hydrogen, or halo; and $R^4$ is $C_1$–$C_6$-alkoxy or aryloxy; or a pharmaceutically acceptable salt thereof; estrogen and a pharmaceutically acceptable carrier.

\* \* \* \* \*